United States Patent
Okuya et al.

(10) Patent No.: US 10,001,557 B2
(45) Date of Patent: Jun. 19, 2018

(54) STATE RECOGNIZING DEVICE, STATE RECOGNIZING METHOD, AND RECORDING MEDIUM

(71) Applicant: Oki Electric Industry Co., Ltd., Tokyo (JP)

(72) Inventors: Daisuku Okuya, Tokyo (JP); Kurato Maeno, Tokyo (JP); Michiyo Matsui, Tokyo (JP)

(73) Assignee: Oki Electric Industry Co., Ltd., Tokyo (JP)

( * ) Notice: Subject to any disclaimer, the term of this patent is extended or adjusted under 35 U.S.C. 154(b) by 365 days.

(21) Appl. No.: 14/773,709

(22) PCT Filed: Oct. 22, 2013

(86) PCT No.: PCT/JP2013/078541
§ 371 (c)(1),
(2) Date: Sep. 8, 2015

(87) PCT Pub. No.: WO2014/141519
PCT Pub. Date: Sep. 18, 2014

(65) Prior Publication Data
US 2016/0025847 A1     Jan. 28, 2016

(30) Foreign Application Priority Data
Mar. 13, 2013   (JP) ................. 2013-050188

(51) Int. Cl.
*G01S 13/58* (2006.01)
*G01V 3/12* (2006.01)
(Continued)

(52) U.S. Cl.
CPC .............. *G01S 13/58* (2013.01); *G01S 7/415* (2013.01); *G01V 3/12* (2013.01); *A61B 5/0205* (2013.01);
(Continued)

(58) Field of Classification Search
CPC .......... G01S 7/292; G01S 13/50; G01S 13/52; G01S 13/5244; G01S 13/526; G01S 13/53; A61B 8/00; A61B 5/0205
(Continued)

(56) References Cited

U.S. PATENT DOCUMENTS 3,796,208 A * 3/1974 Bloice .................. A61B 5/0507
                                                        340/573.1
4,513,748 A * 4/1985 Nowogrodzki ...... A61B 5/1126
                                                        600/430
(Continued)

FOREIGN PATENT DOCUMENTS

JP   2004-174168 A   6/2004
JP   2008-242687 A   10/2008
(Continued)

*Primary Examiner* — Peter M Bythrow
(74) *Attorney, Agent, or Firm* — Rabin & Berdo, P.C.

(57) ABSTRACT

Provided is a state recognizing device including: a first filter unit performing a filtering process on a time-series signal obtained by performing remote measuring on a space, in accordance with a first cutoff frequency to allow a signal component deriving from movement of a biological organism to pass through; a second filter unit performing a filtering process on the time-series signal in accordance with a second cutoff frequency to allow a signal component based on biological information to pass through; an amplitude-component extracting unit extracting a first feature quantity related to an amplitude component from a signal passed through the first and/or second filter units; a frequency-component extracting unit extracting a second feature quantity related to a frequency component from a signal passed through the first and/or second filter units; and a recognizing unit recognizing a state of the space by using the first and second feature quantities.

12 Claims, 4 Drawing Sheets

(51) Int. Cl.

| | |
|---|---|
| *G01S 7/41* | (2006.01) |
| *G01S 13/53* | (2006.01) |
| *G01S 13/526* | (2006.01) |
| *A61B 5/0205* | (2006.01) |
| *G01S 13/52* | (2006.01) |
| *G01S 13/524* | (2006.01) |
| *A61B 8/00* | (2006.01) |
| *G01S 7/292* | (2006.01) |
| *G01S 13/50* | (2006.01) |

(52) U.S. Cl.
CPC ............. *A61B 8/00* (2013.01); *G01S 7/292* (2013.01); *G01S 13/50* (2013.01); *G01S 13/52* (2013.01); *G01S 13/526* (2013.01); *G01S 13/5244* (2013.01); *G01S 13/53* (2013.01)

(58) Field of Classification Search
USPC .......................................................... 342/28
See application file for complete search history.

(56) References Cited

U.S. PATENT DOCUMENTS

| | | | | |
|---|---|---|---|---|
| 4,958,638 A | * | 9/1990 | Sharpe ................ A61B 5/0205 600/407 |
| 5,361,070 A | * | 11/1994 | McEwan ............... A61B 5/0507 342/21 |
| 5,507,291 A | * | 4/1996 | Stirbl .................. A61B 5/0059 600/301 |
| 5,544,661 A | * | 8/1996 | Davis ................... A61B 5/0002 128/904 |
| 5,573,012 A | * | 11/1996 | McEwan ................ A61B 5/024 600/428 |
| 6,062,216 A | * | 5/2000 | Corn ...................... A61B 5/113 128/204.23 |
| 6,132,371 A | * | 10/2000 | Dempsey ............. A61B 5/0006 600/300 |
| 6,239,736 B1 | * | 5/2001 | McDonald ............ G01S 7/2922 340/554 |
| 6,454,708 B1 | * | 9/2002 | Ferguson ........... A61B 5/02055 128/903 |
| 6,456,231 B1 | * | 9/2002 | McEwan ............... G01S 7/2927 342/159 |
| 6,466,125 B1 | * | 10/2002 | Richards ................ G01S 13/42 340/573.1 |
| 6,544,174 B2 | * | 4/2003 | West ..................... A61B 5/1113 128/903 |
| 6,661,345 B1 | * | 12/2003 | Bevan .................... G08B 21/06 340/575 |
| 7,106,885 B2 | * | 9/2006 | Osterweil ............ G08B 21/043 340/573.7 |
| 7,196,629 B2 | * | 3/2007 | Ruoss .................. A61B 5/0507 280/734 |
| 7,272,431 B2 | * | 9/2007 | McGrath ................ A61B 5/024 600/509 |
| 7,345,618 B1 | * | 3/2008 | Cole ....................... G01S 13/32 342/22 |
| 7,567,200 B1 | * | 7/2009 | Osterweil ............ A61B 5/1117 340/573.1 |
| 7,916,066 B1 | * | 3/2011 | Osterweil .......... A61B 15/1117 340/573.1 |
| 8,068,051 B1 | * | 11/2011 | Osterweil ............ A61B 5/1117 340/573.1 |
| 9,000,973 B2 | * | 4/2015 | Hyde ...................... G01S 7/412 340/573.1 |
| 9,568,594 B2 | * | 2/2017 | Harash .................. G01S 7/411 |
| 2002/0120184 A1 | * | 8/2002 | Beck .................... A61B 5/0006 600/300 |
| 2003/0135097 A1 | * | 7/2003 | Wiederhold ........ A61B 5/02055 600/301 |
| 2006/0001545 A1 | * | 1/2006 | Wolf ...................... A47K 3/001 340/573.1 |
| 2006/0195050 A1 | * | 8/2006 | Alwan ................. A61B 5/1038 600/595 |
| 2007/0030115 A1 | * | 2/2007 | Itsuji .................... A61B 5/1171 340/5.8 |
| 2007/0100666 A1 | * | 5/2007 | Stivoric ............... A61B 5/0008 705/3 |
| 2008/0119716 A1 | * | 5/2008 | Boric-Lubecke .... A61B 5/0205 600/407 |
| 2008/0275349 A1 | * | 11/2008 | Halperin ............. A61B 5/0205 600/484 |
| 2008/0287817 A1 | * | 11/2008 | Stivoric ............... A61B 5/0205 600/508 |
| 2009/0017910 A1 | * | 1/2009 | Rofougaran ............ G01S 7/412 463/36 |
| 2010/0026550 A1 | * | 2/2010 | Rosenbury ......... A61B 5/02438 342/22 |
| 2010/0130873 A1 | * | 5/2010 | Yuen .................... A61B 5/0205 600/484 |
| 2010/0141443 A1 | * | 6/2010 | Romero ................. G01S 13/04 340/551 |
| 2010/0198083 A1 | * | 8/2010 | Lin ........................... A61B 5/05 600/484 |
| 2010/0240999 A1 | * | 9/2010 | Droitcour ................ A61B 5/05 600/453 |
| 2011/0240750 A1 | | 10/2011 | Tokura |

FOREIGN PATENT DOCUMENTS

| | | |
|---|---|---|
| JP | 2009-122967 A | 6/2009 |
| JP | 2010-148829 A | 7/2010 |
| JP | 2010-178933 A | 8/2010 |
| JP | 2011-015887 A | 1/2011 |
| JP | 2011-215031 A | 10/2011 |
| JP | 2012-005745 A | 1/2012 |

* cited by examiner

FIG.1

STATE RECOGNIZING DEVICE, STATE RECOGNIZING METHOD, AND RECORDING MEDIUM

TECHNICAL FIELD

The present invention relates to state recognizing devices, state recognizing methods, and recording media.

BACKGROUND ART

For example, Patent Literatures 1 to 4 disclose technologies for recognizing the state of a human in a specific area, such as inside a room, or the presence of a human in a room by using a human sensor. The technologies disclosed in Patent Literatures 1 and 2 involve, for example, detecting the presence of a human in a room based on body movement or biological information obtained from a sensor. Patent Literature 1 discloses a technology for estimating the state of the room from three states, namely, absent, resting, and active states, by performing a threshold determination process based on the intensity of a signal of a Doppler sensor radiated into the room and a variance value. Patent Literature 2 discloses a technology for extracting a respiration component, a heartbeat component, and a body-movement component by performing frequency conversion and a filtering process on a signal from a pressure sensor attached to a life support device so as to detect the absence or presence from these components or to detect an emergency situation.

Patent Literatures 3 and 4 disclose technologies for differentiating sleeping states and performing problem detection intended for performing monitoring during sleeping. Patent Literature 3 discloses a technology for detecting, for example, respiration, a roll-over, or a fall-off from a bed by radiating a signal from a Doppler sensor toward a human sleeping on the bed and then performing a threshold determination process based on information such as an operating time, speed, and direction obtained from the Doppler signal. Patent Literature 4 discloses a technology in which frequency conversion is performed on a binary signal, which indicates whether or not there is a response from a sensor within a certain short period of time, by using, for example, an infrared human sensor, and it is determined whether a human is in a sleeping state, an awakened state, or an absent state based on a period of the signal.

CITATION LIST

Patent Literature

Patent Literature 1: JP 2011-215031A
Patent Literature 2: JP 2004-174168A
Patent Literature 3: JP 2012-5745A
Patent Literature 4: JP 2008-242687A

SUMMARY OF INVENTION

Technical Problem

However, the technologies disclosed in Patent Literatures 1 to 3 are problematic in that, since only a part of the biological information of the human, such as the signal intensity, the variance, the frequency component, and the speed relative to the sensor, is used, it is difficult to accurately recognize the state of the room.

In the technology disclosed in Patent Literature 1, although a threshold value is set based on variance values of the past several tens of seconds, the precision is dependent on the threshold value and the setting method therefor is not clear. The technology disclosed in Patent Literature 2 is problematic in that, since a combination of a biological-information detection sensor, such as an infrared human sensor, and a biological-information detection sensor, such as a pressure sensor, is necessary and the biological information is detected locally, the number of sensors installed inside the room increases, and the system becomes complicated.

With regard to the technology disclosed in Patent Literature 3, since the technology is specialized for monitoring a human on a bed, human respiration or body movement can be extracted with respect to the limited space on the bed. However, in view of applying the technology to a wide range, such as the entire interior of the room, the technology is problematic in that differentiation from external disturbance is not taken into consideration. With regard to the technology disclosed in Patent Literature 4, in order to obtain a respiration cycle, frequency conversion using data for a certain extended period of time is necessary. Although Patent Literature 4 discloses utilization of short-time Fourier transform for a 90 minute period, the technology is problematic in that it cannot handle a change in the state in a short period of time.

In view of the problems mentioned above, an object of the present invention is to provide a new and improved state recognizing device, state recognizing method, and recording medium that can detect the biological condition of a human in a noncontact manner, select a feature quantity with which the state within a predetermined space can be distinguished, and recognize the state of the space more accurately based on the selected feature quantity.

Solution to Problem

According to an aspect of the present invention in order to solve the above-mentioned problem, there is provided a state recognizing device including: a first filter unit that performs a filtering process on a time-series signal, which is obtained as a result of performing remote measuring on a space, in accordance with a first cutoff frequency so as to allow a signal component deriving from movement of a biological organism to pass through; a second filter unit that performs a filtering process on the time-series signal in accordance with a second cutoff frequency, which is different from the first cutoff frequency, so as to allow a signal component based on biological information of the biological organism to pass through; an amplitude-component extracting unit that extracts a first feature quantity related to an amplitude component from a signal passed through the first filter unit and/or the second filter unit; a frequency-component extracting unit that extracts a second feature quantity related to a frequency component from a signal passed through the first filter unit and/or the second filter unit; and a recognizing unit that recognizes a state of the space by using the first feature quantity and the second feature quantity.

The frequency-component extracting unit may perform frequency conversion on the signal passed through the first filter unit and/or the second filter unit and set a sum of spectrum intensity after the frequency conversion as the second feature quantity.

The frequency-component extracting unit may apply a band-pass filter to the signal passed through the first filter unit and/or the second filter unit and set a signal value after applying the band-pass filter as the second feature quantity.

The frequency-component extracting unit may set the total number of times the signal passed through the first filter unit and/or the second filter unit crosses over a zero point as the second feature quantity.

The amplitude-component extracting unit may calculate an instantaneous amplitude of the signal passed through the first filter unit and/or the second filter unit and set a representative value equivalent to a time window of the instantaneous amplitude as the first feature quantity.

The representative value may be at least one of an average value, a median value, a mode value, variance, standard deviation, a maximum value, a minimum value, and spectrum intensity after performing frequency conversion on the signal passed through the first filter unit.

The recognizing unit may recognize at least one of an absent state, a present state, a resting state, and an active state as the state of the space.

The state recognizing device may further includes: a detecting unit that performs remote measuring of the space and outputs the time-series signal.

The state recognizing device may further includes: a preprocessing unit that performs predetermined signal processing before the time-series signal output from the detecting unit is passed through the first filter unit and the second filter unit.

The preprocessing unit may perform offset adjustment on the time-series signal.

According to another aspect of the present invention in order to solve the above-mentioned problem, there is provided a state recognizing method including: a first filtering step for performing a filtering process on a time-series signal, which is obtained as a result of performing remote measuring on a space, in accordance with a first cutoff frequency so as to allow a signal component deriving from movement of a biological organism to pass through; a second filtering step for performing a filtering process on the time-series signal in accordance with a second cutoff frequency, which is different from the first cutoff frequency, based on biological information of the biological organism; an amplitude-component extracting step for extracting a first feature quantity related to an amplitude component from a signal passed in the first filtering step and/or the second filtering step; a frequency-component extracting step for extracting a second feature quantity related to a frequency component from a signal passed in the first filtering step and/or the second filtering step; and a state recognizing step for recognizing a state of the space by using the first feature quantity and the second feature quantity.

According to another aspect of the present invention in order to solve the above-mentioned problem, there is provided a recording medium having a computer program stored therein, the computer program causing a computer to execute: a first filtering step for performing a filtering process on a time-series signal, which is obtained as a result of performing remote measuring on a space, in accordance with a first cutoff frequency so as to allow a signal component deriving from movement of a biological organism to pass through; a second filtering step for performing a filtering process on the time-series signal in accordance with a second cutoff frequency, which is different from the first cutoff frequency, based on biological information of the biological organism; an amplitude-component extracting step for extracting a first feature quantity related to an amplitude component from a signal passed in the first filtering step and/or the second filtering step; a frequency-component extracting step for extracting a second feature quantity related to a frequency component from a signal passed in the first filtering step and/or the second filtering step; and a state recognizing step for recognizing a state of the space by using the first feature quantity and the second feature quantity.

Advantageous Effects of Invention

According to the present invention described above, there can be provided a new and improved state recognizing device, state recognizing method, and recording medium that can detect the biological condition of a human in a noncontact manner, select a feature quantity with which the state within a predetermined space can be distinguished, and recognize the state of the space more accurately based on the selected feature quantity.

DESCRIPTION OF EMBODIMENTS

Hereinafter, referring to the appended drawings, a preferred embodiment of the present invention will be described in detail. It should be noted that, in this specification and the appended drawings, structural elements that have substantially the same function and structure are denoted with the same reference numerals, and repeated explanation thereof is omitted.

1. Embodiment of Present Invention

First, the configuration of a state recognizing device 100 according to an embodiment of the present invention will be described with reference to the drawings.

Figure 1:
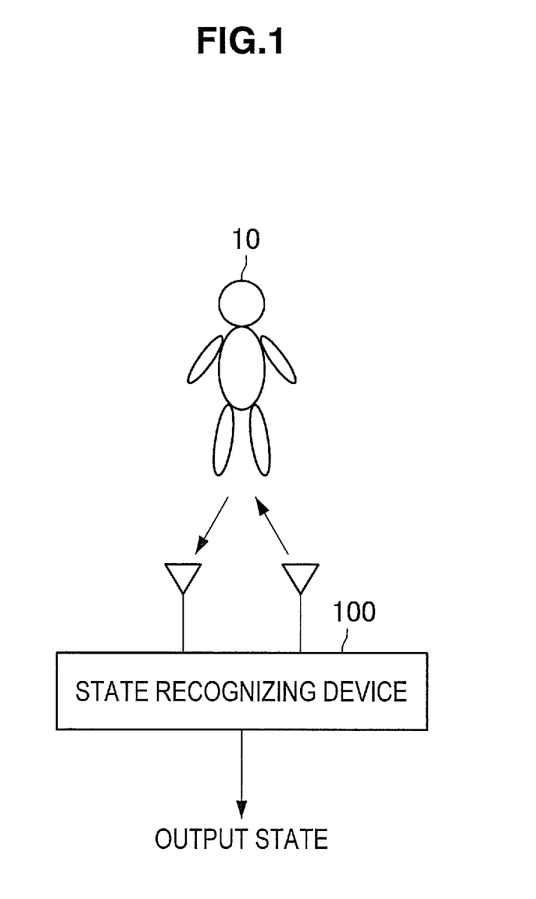
FIG. 1 illustrates the configuration of a state recognizing device 100 according to an embodiment of the present invention.

FIG. 1 illustrates the configuration of the state recognizing device 100 according to an embodiment of the present invention. As shown in FIG. 1, the state recognizing device 100 is a device that detects the presence or absence of a human 10 as well as the state of the human 10.

The human 10 is a reflective object that reflects an electric wave or an ultrasonic wave radiated from a Doppler sensor. There may be a plurality of humans 10. An object whose presence or absence or whose state is to be determined by the state recognizing device 100 is not limited to a human 10 and may be an animal or another non-periodic moving object. Based on a Doppler signal, which is a frequency signal corresponding to a difference between an electric wave radiated from the Doppler sensor and an electric wave reflected by a reflective object present within a detection area, the state recognizing device 100 detects whether or not a human 10, an animal, or another non-periodic moving object is present as a reflective object, that is, the presence or absence of a non-periodic moving object.

An embodiment of the present invention relates to the state recognizing device 100, and particularly, to a recognizing process for recognizing the presence or absence of a human 10 as well as the state of the human 10.

Functional Configuration Example of State Recognizing Device

Figure 2:
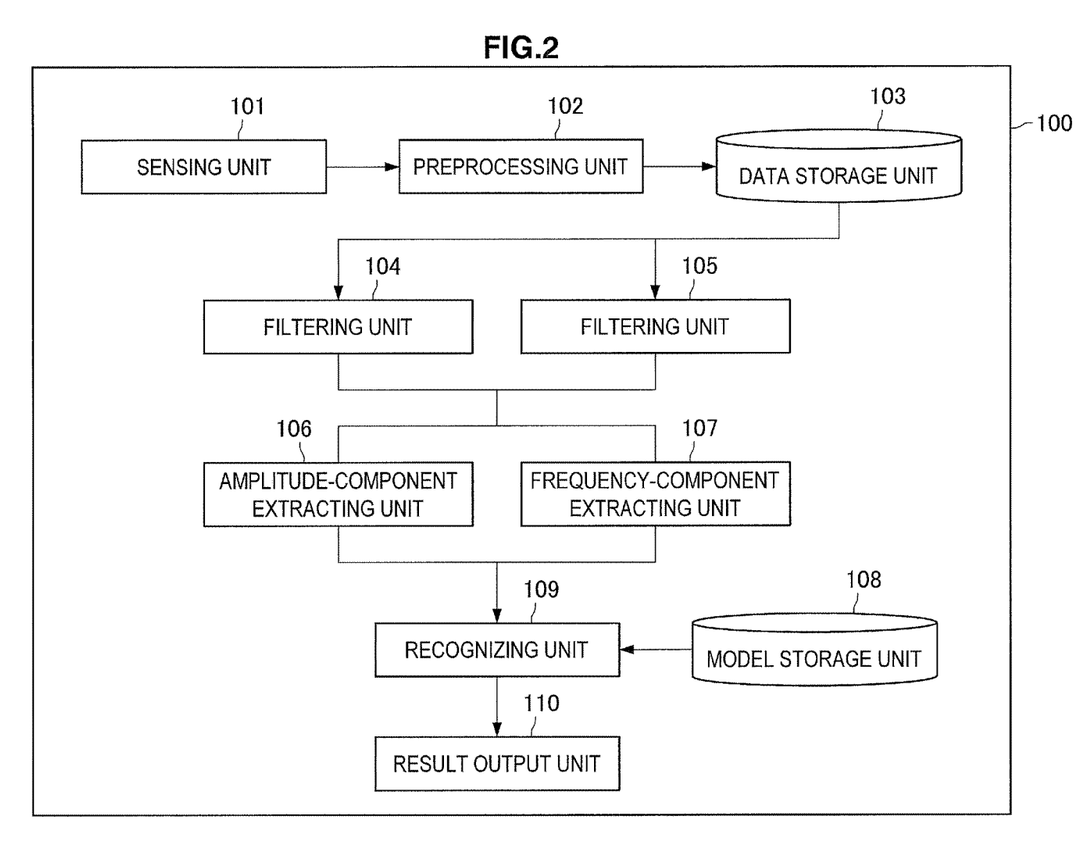
FIG. 2 illustrates a functional configuration example of the state recognizing device 100 according to an embodiment of the present invention.

Next, a functional configuration example of a state recognizing device according to an embodiment of the present invention will be described with reference to the drawings. FIG. 2 illustrates the functional configuration example of the state recognizing device 100 according to an embodiment of the present invention. The functional configuration example of the state recognizing device 100 according to an embodiment of the present invention will be described below with reference to FIG. 2.

As shown in FIG. 2, the state recognizing device 100 according to an embodiment of the present invention includes a sensing unit 101, a preprocessing unit 102, a data storage unit 103, filtering units 104 and 105, an amplitude-component extracting unit 106, a frequency-component extracting unit 107, a model storage unit 108, a recognizing unit 109, and a result output unit 110.

The sensing unit 101 detects movement of an object within an area targeted by a sensor. In this embodiment, a Doppler sensor is used as the sensor included in the sensing unit 101. The sensing unit 101 has a configuration of outputting, from a transmission antenna, an output signal from a local oscillator and receiving a reflected wave from a target object via a reception antenna. When the sensing unit 101 receives reflected light from the target object via the reception antenna, the sensing unit 101 uses a distributor to divide a received signal into two signals and uses a phase shifter to delay one of the signals by 90 degrees. Since the reflected wave from the moving object undergoes frequency modulation due to a Doppler effect, a phase difference occurs between the signals.

In this embodiment, the two waves that are obtained by the Doppler sensor and whose phases differ from each other by 90 degrees are defined as $V_I(t)$ and $V_Q(t)$, respectively, as shown in numerical expression 1 below. The subscripts I and Q denote in-phase and quadrature, respectively.

[Math. 1]

$$V_I(t) = A_I \sin\left(\frac{4\pi R(t)}{\lambda} + \phi_0\right) + O_I + w_I \quad \text{(Numerical Expression 1)}$$
$$V_Q = A_Q \sin\left(\frac{4\pi R(t)}{\lambda} + \phi_0 + \frac{\pi}{2}\right) + O_Q + w_Q$$

In numerical expression 1, A denotes an amplitude of each signal, λ denotes a wavelength, R(t) denotes the distance between the Doppler sensor and the target object at a time point t, $\phi_0$ denotes an initial phase, O denotes direct-current offset, and w denotes a noise component. A method of how numerical expression 1 is derived is disclosed in "Droitcour, A. D. et al. "Range correlation and I/Q performance benefits in single-chip silicon Doppler radars for noncontact cardiopulmonary monitoring" Microwave Theory and Techniques, IEEE Transactions, Vol. 52, No. 3, pp. 838-848, March 2004".

The preprocessing unit 102 preprocesses the signals output from the sensing unit 101 before the signals are supplied to the filtering units 104 and 105. The preprocessing executed by the preprocessing unit 102 may include, for example, conversion to digital signals by sampling the signal intensity, offset adjustment of the signals for complying with different types of Doppler sensors, and removal of direct-current components by applying a high-pass filter.

The sensing unit 101 and the preprocessing unit 102 may be realized as separate hardware units or may be realized as a single hardware unit. Furthermore, the preprocessing unit 102 may perform sub-sampling on the supplied signals so as to remove noise components superposed due to supply voltage as well as redundant high-frequency regions, thereby reducing the throughput in subsequent blocks.

The data storage unit 103 stores the Doppler signals that are output from the sensing unit 101 and that have been preprocessed by the preprocessing unit 102. The Doppler signals stored in the data storage unit 103 may be filtered by the filtering units 104 and 105.

The filtering unit 104 filters the Doppler signal stored in the data storage unit 103. In this embodiment, in order to allow only signal components arising from human movement, which are distributed over a relatively wide range, to pass through, the filtering unit 104 may be constituted of, for example, a low-pass filter whose cutoff frequency is set to about several tens of Hz. The Doppler signal that has passed through the filtering unit 104 is sent to the amplitude-component extracting unit 106 and the frequency-component extracting unit 107.

The filtering unit 105 filters the Doppler signal stored in the data storage unit 103. In this embodiment, for example, in order to extract a feature quantity in a frequency band of a signal component based on long periodic movement, such as human respiration, the filtering unit 105 may be constituted of a low-pass filter whose cutoff frequency is set to be lower than that of the filtering unit 104. The Doppler signal that has passed through the filtering unit 105 is sent to the amplitude-component extracting unit 106 and the frequency-component extracting unit 107.

The filtering methods in the filtering units 104 and 105 are not limited to specific methods. The method used in each of the filtering units 104 and 105 may be selected from among a method that employs conversion to a frequency domain based on Fourier transform, an infinite impulse response (IIR) filter, and a finite impulse response (FIR) filter, so long as a digital signal can be filtered.

The amplitude-component extracting unit 106 extracts an amplitude component, which is a feature quantity to be used in a recognizing process in the recognizing unit 109, by using the Doppler signals that have passed through the filtering units 104 and 105. The amplitude-component extracting unit 106 calculates an instantaneous amplitude α(t) in accordance with, for example, numerical expression 2 below by using the signals $V_I(t)$ and $V_Q(t)$ that have passed through the filtering units 104 and 105.

[Math. 2]

$$\alpha(t) = \sqrt{(V_I(t) - D_I(t))^2 + (V_Q(t) - D_Q(t))^2} \quad \text{(Numerical Expression 2)}$$

In numerical expression 2, $D_I(t)$ and $D_Q(t)$ denote direct-current components of an I signal and a Q signal, respectively. If removal of direct-current components has been performed by applying the high-pass filter in the preprocessing by the preprocessing unit 102, both $D_I(t)$ and $D_Q(t)$ in numerical expression 2 can be regarded as zero.

Then, with respect to the instantaneous amplitude α(t) obtained from numerical expression 2, the amplitude-component extracting unit 106 employs a representative value, which is equivalent to a time window in which recognition is to be performed, as an amplitude component. The representative value expressing the amplitude component includes, for example, an average, median, mode, variance, standard deviation, maximum value, minimum value, and maximum spectrum intensity after frequency conversion. The amplitude-component extracting unit 106 sets one of or a plurality of these amplitude-component-expressing representative values as an amplitude component or components. The amplitude-component extracting unit 106 outputs the employed amplitude component or components to the recognizing unit 109.

The frequency-component extracting unit 107 extracts a frequency component, which is a feature quantity to be used in the recognizing process by the recognizing unit 109, by using the Doppler signals that have passed through the filtering units 104 and 105. The frequency-component extracting unit 107 outputs the extracted frequency component to the recognizing unit 109.

The frequency-component extracting unit 107 may extract, for example, spectrum intensity based on Fourier transform as the frequency component. In frequency conversion based on Fourier transform, frequency resolution is dependent on the length of input sequence. Therefore, in order for the frequency-component extracting unit 107 to obtain an appropriate frequency component, data equivalent to a sufficiently large time length is required. For example, if the resolution is set to 0.1 Hz relative to data sampled at 500 Hz, data equivalent to 10 seconds is required to obtain an appropriate frequency component.

As the frequency component, the frequency-component extracting unit 107 may set a sum S of spectrum intensity corresponding to a frequency band (e.g., a frequency band ranging between 0.1 Hz and 1.5 Hz) that contains a large amount of biological information, such as a human respiration component or a human heartbeat component, with respect to a signal sequence after Fourier transform. The frequency-component extracting unit 107 may calculate the sum S of spectrum intensity in accordance with numerical expression 3 below.

[Math. 3]

$$S = \sum_{f=f_{min}}^{f_{max}} p(f) \quad \text{(Numerical Expression 3)}$$

In numerical expression 3, $f_{min}$ denotes a lower frequency limit (e.g., 0.1) of the target frequency band, $f_{max}$ denotes an upper frequency limit (e.g., 1.5) of the target frequency band, and p(f) denotes spectrum intensity at a frequency f.

Although the frequency-component extracting unit 107 determines the sum of spectrum intensity with respect to a signal sequence after Fourier transform in this embodiment, the present invention is not limited to this example. Another method, such as Hadamard transform, cosine transform, Hilbert transform, or discrete wavelet transform, may be used so long as time-series data can be converted into a frequency component with the method.

The frequency-component extracting unit 107 may extract a frequency component with, for example, a band-pass filter. In a case where a band-pass filter is used to extract a frequency component, for example, the frequency-component extracting unit 107 may use a band-pass filter whose cutoff frequencies for the I signal and the Q signal are set to 0.1 Hz and 1.5 Hz, respectively. Then, for each of the I signal and the Q signal obtained after using the band-pass filter, the frequency-component extracting unit 107 may set the amplitude value as the frequency component or may set the sum of squares of the I signal and the Q signal as the frequency component.

The frequency-component extracting unit 107 may extract a frequency component by, for example, calculating the number of crossovers at the zero point. With respect to the signal sequences filtered by the filtering units 104 and 105, the frequency-component extracting unit 107 counts the number of times the I signal and the Q signal cross over the zero point within a certain time period and sets the sum of the number of crossovers as the frequency component. The frequency-component extracting unit 107 may set the number of times each of the I signal and the Q signal crosses over the zero point as the frequency component, may set the sum of the number of times the I signal and the Q signal cross over the zero point as the frequency component, or may convert the I signal and the Q signal into an instantaneous amplitude and set the number of crossovers by that sequence as the frequency component.

The model storage unit 108 stores a model to be used in a state recognizing process by the recognizing unit 109. The model storage unit 108 collects an aggregate of feature quantities corresponding to different states, which are obtained as a result of preprocessing by the preprocessing unit 102, amplitude-component extraction by the amplitude-component extracting unit 106, and frequency-component extraction by the frequency-component extracting unit 107 performed on data that is given an annotation expressing the state within an area and that is acquired by the sensing unit 101. The model storage unit 108 stores the data collected in this manner as teacher data. By using the collected aggregate of feature quantities corresponding to different states, the model storage unit 108 stores a model to be generated in accordance with a state recognizing process at the recognizing unit 109.

The recognizing unit 109 executes a state recognizing process for recognizing the state within a target area by using the feature quantity with respect to the amplitude component output from the amplitude-component extracting unit 106 and the feature quantity with respect to the frequency component output from the frequency-component extracting unit 107. When executing the state recognizing process, the recognizing unit 109 uses the model stored in the model storage unit 108.

The state recognizing process in the recognizing unit 109 may be performed by, for example, determining which feature-quantity aggregate of which state is resembled by the feature quantities acquired from the amplitude-component extracting unit 106 and the frequency-component extracting unit 107 from among the feature-quantity aggregates stored in the model storage unit 108. In the state recognizing process in the recognizing unit 109, for example, a pattern recognizer based on a support vector machine or a hidden Markov model may be used. The recognizing unit 109 outputs, to the result output unit 110, the result of the state recognizing process performed using the feature quantities acquired from the amplitude-component extracting unit 106 and the frequency-component extracting unit 107.

In this embodiment, the recognizing unit 109 determines one of three states, namely, "absent", "resting", and "active" states, within the target area as a recognition result. An "absent" state refers to a state in which there are no humans within the target area, a "resting" state refers to a state in which a human is present within the target area but is only breathing without actively moving (e.g., a state in which a human is sitting on a chair or the floor, a state in which a human is standing, or a state in which a human is sleeping), and an "active" state refers to a state in which a human is present within the target area and is actively moving by, for example, moving limbs (e.g., moving or foot stamping).

In this embodiment, the recognizing unit 109 determines any one of the three states, namely, the "absent", "resting", and "active" states, as a recognition result by using the feature quantities acquired from the amplitude-component extracting unit 106 and the frequency-component extracting unit 107. By using the feature quantities acquired from the amplitude-component extracting unit 106 and the frequency-component extracting unit 107, the recognizing unit 109 is capable of determining one of the above three states, which is difficult to determine accurately in existing technologies.

The result output unit 110 outputs the result of the state recognizing process in the recognizing unit 109 from the state recognizing device 100. The result output unit 110 may output the result of the state recognizing process in the recognizing unit 109 in the form of, for example, text, sound, or an image from the state recognizing device 100.

By having the above configuration, the state recognizing device 100 according to an embodiment of the present invention can detect the biological condition of a human in a noncontact manner, select a feature quantity with which the state within a predetermined space can be distinguished, and recognize the state of the space more accurately based on the selected feature quantity.

The functional configuration example of the state recognizing device 100 according to an embodiment of the present invention has been described above. Next, an operational example of the state recognizing device 100 according to an embodiment of the present invention will be described.

Operational Example of State Recognizing Device

Figure 3:
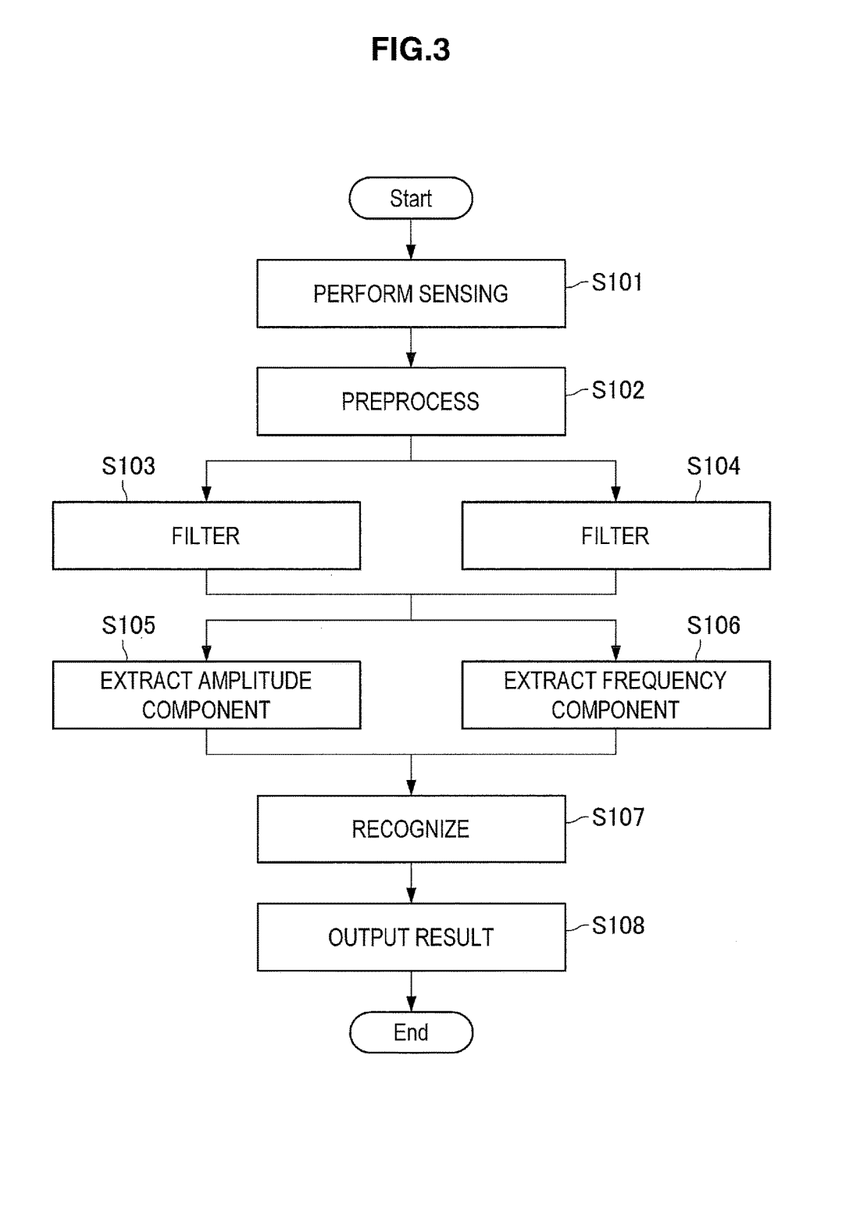
FIG. 3 is a flowchart illustrating an operational example of the state recognizing device 100 according to an embodiment of the present invention.

FIG. 3 is a flowchart illustrating an operational example of the state recognizing device 100 according to an embodiment of the present invention. The flowchart shown in FIG. 3 corresponds to an operational example where the state recognizing device 100 according to an embodiment of the present invention recognizes the state within a predetermined space by using data acquired by the sensing unit 101. The operational example of the state recognizing device 100 according to an embodiment of the present invention will be described below with reference to FIG. 3.

The state recognizing device 100 according to an embodiment of the present invention causes the sensing unit 101 to sense movement within a target area (step S101). As described above, in this embodiment, a Doppler sensor is used as the sensor included in the sensing unit 101. Furthermore, when performing sensing, the sensing unit 101 outputs, from a transmission antenna, an output signal from a local oscillator and receives a reflected wave from a target object via a reception antenna. Then, the sensing unit 101 uses a distributor to divide a received signal into two signals and uses a phase shifter to delay one of the signals by 90 degrees, thereby obtaining an I signal and a Q signal.

When movement in the target area is sensed by the sensing unit 101 in step S101 described above, the state recognizing device 100 according to an embodiment of the present invention subsequently causes the preprocessing unit 102 to preprocess the signals obtained as a result of sensing (step S102). As described above, the preprocessing executed by the preprocessing unit 102 may include, for example, conversion to digital signals by sampling the signal intensity, offset adjustment of the signals for complying with different types of Doppler sensors, and removal of direct-current components by applying a high-pass filter. Furthermore, the preprocessing in step S102 may include performing sub-sampling on the signals so as to remove noise components superposed due to supply voltage as well as redundant high-frequency regions.

When the I signal and the Q signal are preprocessed by the preprocessing unit 102 in step S102 described above, the preprocessed I signal and Q signal are stored into the data storage unit 103.

Furthermore, when the I signal and the Q signal are preprocessed by the preprocessing unit 102 in step S102 described above, the state recognizing device 100 according to an embodiment of the present invention subsequently causes the filtering unit 104 to filter the preprocessed I signal and Q signal (step S103). As described above, in order to allow only signal components arising from human movement, which are distributed over a relatively wide range, to pass through, the filtering unit 104 may be constituted of, for example, a low-pass filter whose cutoff frequency is set to about several tens of Hz. In the case where the filtering unit 104 has such a configuration, only signal components arising from human movement pass through as a result of the filtering in step S103.

When the I signal and the Q signal are preprocessed by the preprocessing unit 102 in step S102 described above, the state recognizing device 100 according to an embodiment of the present invention subsequently causes the filtering unit 105 to filter the preprocessed I signal and Q signal concurrently with the filtering in step S103 (step S104). As described above, for example, in order to extract a feature quantity in a frequency band of a signal component based on long periodic movement, such as human respiration or human heartbeat, the filtering unit 105 may be constituted of a low-pass filter whose cutoff frequency is set to be lower than that of the filtering unit 104. In the case where the filtering unit 105 has such a configuration, only signal components based on long periodic movement, such as human respiration or human heartbeat, pass through as a result of the filtering in step S103.

When the I signal and the Q signal are filtered in step S103 and step S104 described above, the state recognizing device 100 according to an embodiment of the present invention subsequently causes the amplitude-component extracting unit 106 to extract an amplitude component, which is a feature quantity to be used in the recognizing process by the recognizing unit 109, by using the filtered signals (step S105). As described above, the amplitude-component extracting unit 106 calculates an instantaneous amplitude $\alpha(t)$ in accordance with numerical expression 2 mentioned above and employs a representative value, which is equivalent to a time window in which recognition is to be performed, as an amplitude component with respect to the instantaneous amplitude $\alpha(t)$ obtained in accordance with numerical expression 2.

Furthermore, the state recognizing device 100 according to an embodiment of the present invention causes the frequency-component extracting unit 107 to extract a frequency component, which is a feature quantity to be used in the recognizing process by the recognizing unit 109, by using the filtered signals concurrently with the amplitude-component extracting process in step S105 described above (step S106).

As described above, the frequency-component extracting unit 107 may extract a frequency component, which is a feature quantity to be used in the recognizing process by the recognizing unit 109, in accordance with, for example, spectrum intensity based on Fourier transform, application of a band-pass filter, or calculation of the number of crossovers at the zero point.

When the amplitude component is extracted in step S105 described above and the frequency component is extracted in step S106 described above, the state recognizing device 100 according to an embodiment of the present invention subsequently causes the recognizing unit 109 to recognize the state within the target area by using the extracted amplitude component and frequency component (step S107). As described above, the recognizing process in step S107 may be performed by, for example, determining a resemblance with respect to a feature-quantity aggregate of whichever one of states from among the feature-quantity aggregates stored in the model storage unit 108. Specifically, in the recognizing process in step S107, for example, a pattern recognizer based on a support vector machine or a hidden Markov model may be used.

As described above, in this embodiment, one of three states, namely, "absent", "resting", and "active" states, as the state within the target area is determined as a recognition result in the recognizing process in step S107.

When the state within the target area is determined as a result of the recognizing process in step S107, the state recognizing device 100 according to an embodiment of the present invention subsequently outputs the result of the state recognizing process in the recognizing unit 109 to the result output unit 110 (step S108). As described above, the result output unit 110 may output the result of the state recognizing process in the recognizing unit 109 in the form of, for example, text, sound, or an image from the state recognizing device 100.

By executing the above operation, the state recognizing device 100 according to an embodiment of the present invention can detect the biological condition of a human in a noncontact manner, select a feature quantity with which the state within a predetermined space can be distinguished, and recognize the state of the space more accurately based on the selected feature quantity.

A difference between the recognizing process by the state recognizing device 100 according to an embodiment of the present invention and a state recognizing process in the related art will now be described.

Figure 4:
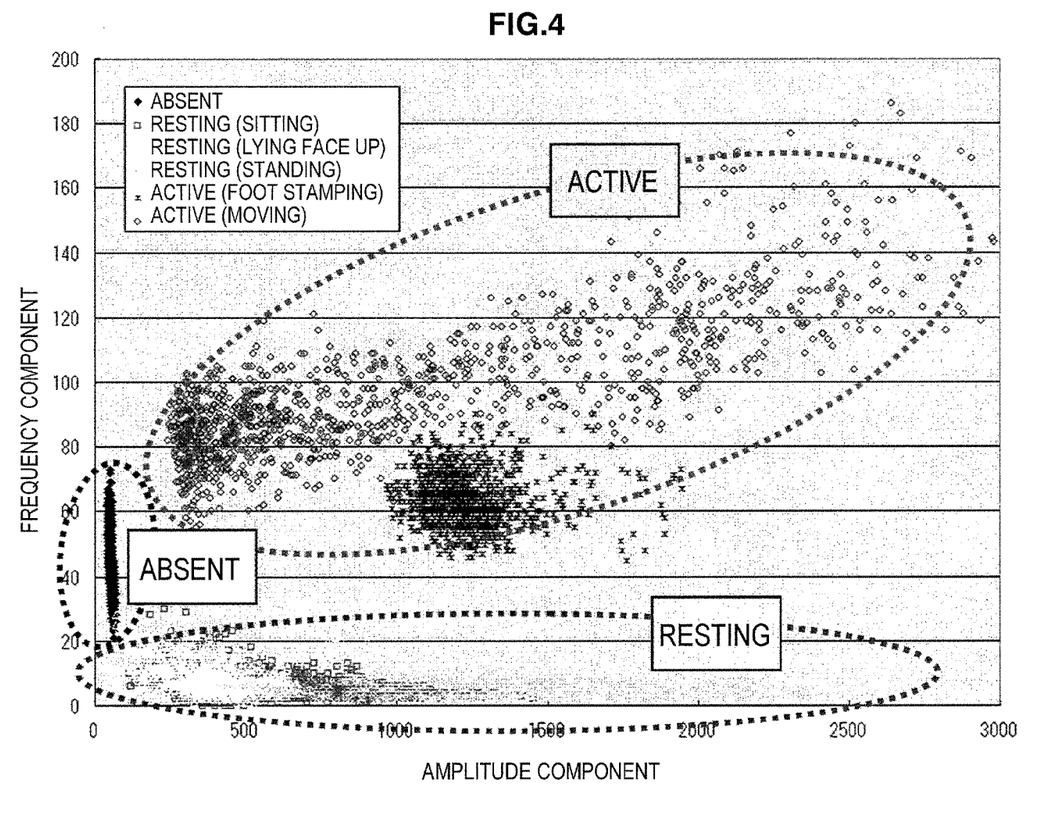
FIG. 4 illustrates a plotted graph showing distribution of amplitude components and frequency components of data obtained by a Doppler sensor.

FIG. 4 illustrates a plotted graph showing distribution of amplitude components and frequency components of data obtained by the Doppler sensor. FIG. 4 shows the distributively-plotted amplitude components and frequency components of data obtained by the Doppler sensor when a single person present in an observation range of the Doppler sensor is made to perform "sitting", "lying face up", "standing", "foot stamping", and "moving" actions and also when there is no one present in the observation range of the Doppler sensor.

The "sitting", "lying face up", and "standing" actions correspond to the "resting" state within the area in the above embodiment since there is little movement other than breathing. The "foot stamping" and "moving" actions correspond to the "active" state within the area in the above embodiment since there is movement involving movement of limbs.

The invention disclosed in Patent Literature 1 described above recognizes the state within an area by using only signal intensity and its variance. However, if the state is to be recognized by using the invention disclosed in Patent Literature 1 when distribution of amplitude components and frequency components as shown in FIG. 4 is obtained, "active" amplitude components and "resting" amplitude components are widely distributed, and the distribution ranges substantially overlap each other, thus making it difficult to accurately distinguish them from each other.

The invention disclosed in Patent Literature 2 described above recognizes the state within an area by using a frequency component. However, if the state is to be recognized by using the invention disclosed in Patent Literature 2 when distribution of amplitude components and frequency components as shown in FIG. 4 is obtained, there is a region where the distribution range of "absent" frequency components and the distribution range of "active" amplitude components overlap each other, thus making it difficult to accurately distinguish them from each other in that region.

In contrast, the state recognizing device 100 according to this embodiment recognizes the state within an area by using both an amplitude component and a frequency component. Therefore, the state recognizing device 100 according to this embodiment is capable of distinguishing the "absent" state and a state other than the "absent" state from each other based on an amplitude component and is also capable of distinguishing the "resting" state and the "active" state from each other based on a frequency component.

Consequently, the state recognizing device 100 according to this embodiment recognizes the state within an area by using both an amplitude component and a frequency component so as to be capable of distinguishing the "absent" state and a state other than the "absent" state from each other, which is difficult in the technologies in the related art, and also distinguishing the "resting" state and the "active" state from each other in a case of a state other than the "absent" state.

In the state recognizing device 100 according to an embodiment of the present invention, the model storage unit 108 stores the data as shown in FIG. 4, and the recognizing unit 109 refers to the data stored in the model storage unit 108, so that state recognition using both an amplitude component and a frequency component becomes possible.

The state recognizing device 100 according to this embodiment may notify a user of the state within a recognition target area in detail by operating in cooperation with another system. For example, in a case where a system that automatically locks entrance and exit doors of a recognition target area is provided, if the state recognizing device 100 determines that the state within the area is the "absent" state regardless of the fact that there is someone inside, the state recognizing device 100 may operate in cooperation with the locking system to provide a notification that a problem has occurred in the person inside.

2. Conclusion

As described above, an embodiment of the present invention provides a state recognizing device 100 that filters signals, which are obtained as a result of performing sensing in an area, for obtaining an amplitude component and a frequency component to be used for accurately recognizing the state of the area, and that obtains an amplitude component and a frequency component from the filtered signals.

By obtaining the amplitude component and the frequency component, the state recognizing device 100 according to an embodiment of the present invention can identify whether or not the state is an absent state, which is difficult to identify based on a frequency component alone, and can also identify whether or not the state is a resting state, which is difficult to identify based on an amplitude component alone.

The steps in the process executed by the state recognizing device 100 described above do not necessarily have to be processed in a time-series manner in the chronological order described in the flowchart. For example, the steps in the process executed by the state recognizing device 100 may be processed in an order different from the order described in the flowchart or may be processed concurrently.

Furthermore, a computer program for causing hardware, such as a CPU, a ROM, and a RAM, contained in the state recognizing device 100 described above described above to exhibit a function similar to the configuration of the state recognizing device 100 described above may be created. Moreover, a storage medium having the aforementioned computer program stored therein may be provided. Furthermore, the functional blocks shown in the functional block diagram may be constituted by hardware so that a series of processes can be realized with the hardware.

Heretofore, a preferred embodiment of the present invention has been described in detail with reference to the appended drawings, but the present invention is not limited thereto. It should be understood by those skilled in the art that various changes and alterations may be made without departing from the spirit and scope of the appended claims and belong to the technical scope of the invention.

For example, although the sensing unit 101 and the data storage unit 103 are included within the state recognizing device 100 in the above embodiment, the present invention is not limited to this example. For example, the sensing unit 101 and the data storage unit 103 may be provided outside the state recognizing device 100, and data stored in the data storage unit 103 may be analyzed by the state recognizing device 100, so that the state of a target area may be recognized based on data obtained by the sensing unit 101.

Furthermore, the state recognizing device 100 according to an embodiment of the present invention may execute the recognizing process immediately after the sensing unit 101 outputs a signal, or may store the signal output from the sensing unit 101 into the data storage unit 103 and execute the recognizing process afterwards.

Furthermore, for example, although the state recognizing device 100 recognizes three states, namely, "absent", "resting", and "active" states, in the above embodiment, the state recognizing device 100 may simply recognize one of two states, namely, "absent" and "present" states, and the recognized state may be output as a recognition result from the result output unit 110.

Furthermore, for example, the amplitude-component extracting unit 106 may extract an amplitude component by using only a signal filtered by the filtering unit 104. Moreover, for example, the frequency-component extracting unit 107 may extract an amplitude component by using only a signal filtered by the filtering unit 106.

Furthermore, for example, an object whose state is to be recognized by the state recognizing device 100 is not limited to a human. An object whose state is to be recognized by the state recognizing device 100 may include another biological organism in addition to a human so long as biological information, such as respiration or heartbeat information, can be acquired by the sensing unit 101 together with information deriving from movement of the biological organism.

REFERENCE SIGNS LIST 100 state recognizing device
101 sensing unit
102 preprocessing unit
103 data storage unit
104, 105 filtering unit
106 amplitude-component extracting unit
107 frequency-component extracting unit
108 model storage unit
109 recognizing unit
110 result output unit

The invention claimed is:

1. A state recognizing device for recognizing a plurality of states of a space, comprising:
   a first filter unit that performs a filtering process on a time-series signal, which is obtained as a result of performing remote measuring on the space, in accordance with a first cutoff frequency so as to allow a signal component deriving from movement of a biological organism to pass through;
   a second filter unit that performs a filtering process on the time-series signal in accordance with a second cutoff frequency, which is lower than the first cutoff frequency, so as to allow a signal component based on biological information of the biological organism to pass through;
   an amplitude-component extracting unit that extracts a first feature quantity related to an amplitude component from a signal passed through the first filter unit and the second filter unit;
   a frequency-component extracting unit that extracts a second feature quantity related to a frequency component from a signal passed through the first filter unit and the second filter unit;
   a model storage unit that collects an aggregate of feature quantity-state data, each piece of the feature quantity-state data including amplitude information corresponding to an output of the amplitude-component extracting unit, frequency information corresponding to an output of the frequency-component extracting unit, and one of the plurality of the sates for the amplitude information and the frequency information; and
   a recognizing unit that recognizes a state of the space by using the first feature quantity, the second feature quantity, and the aggregate of feature quantity-state data.

2. The state recognizing device according to claim 1, wherein the frequency-component extracting unit performs frequency conversion on the signal passed through the first filter unit and the second filter unit and sets a sum of spectrum intensity after the frequency conversion as the second feature quantity.

3. The state recognizing device according to claim 1, wherein the frequency-component extracting unit applies a band-pass filter to the signal passed through the first filter unit and the second filter unit and sets a signal value after applying the band-pass filter as the second feature quantity.

4. The state recognizing device according to claim 1, wherein the frequency-component extracting unit sets the total number of times the signal passed through the first filter unit and the second filter unit crosses over a zero point as the second feature quantity.

5. The state recognizing device according to claim 1, wherein the amplitude-component extracting unit calculates an instantaneous amplitude of the signal passed through the first filter unit and the second filter unit and sets a representative value equivalent to a time window of the instantaneous amplitude as the first feature quantity.

6. The state recognizing device according to claim 5, wherein the representative value is at least one of an average value, a median value, a mode value, variance, standard deviation, a maximum value, a minimum value, and spectrum intensity after performing frequency conversion on the signal passed through the first filter unit and the second filter unit.

7. The state recognizing device according to claim 1, wherein the plurality of states include at least one of an absent state, a present state, a resting state, and an active state.

8. The state recognizing device according to claim 1, further comprising:
a detecting unit that performs remote measuring of the space and outputs the time-series signal.

9. The state recognizing device according to claim 8, further comprising:
a preprocessing unit that performs predetermined signal processing before the time-series signal output from the detecting unit is passed through the first filter unit and the second filter unit.

10. The state recognizing device according to claim 9, wherein the preprocessing unit performs offset adjustment on the time-series signal.

11. A state recognizing method for recognizing a plurality of states of a space, comprising:
a first filtering step for performing a filtering process on a time-series signal, which is obtained as a result of performing remote measuring on the space, in accordance with a first cutoff frequency so as to allow a signal component deriving from movement of a biological organism to pass through;
a second filtering step for performing a filtering process on the time-series signal in accordance with a second cutoff frequency, which is lower than the first cutoff frequency, based on biological information of the biological organism;
an amplitude-component extracting step for extracting a first feature quantity related to an amplitude component from a signal passed in the first filtering step and the second filtering step;
a frequency-component extracting step for extracting a second feature quantity related to a frequency component from a signal passed in the first filtering step and the second filtering step;
a model storing step for collecting an aggregate of feature quantity-state data, each piece of the feature quantity-state data including amplitude information corresponding to an output of the amplitude-component extracting unit, frequency information corresponding to an output of the frequency-component extracting unit, and one of the plurality of the sates for the amplitude information and the frequency information; and
a state recognizing step for recognizing a state of the space by using the first feature quantity, the second feature quantity, and the aggregate of feature quantity-state data.

12. A non-transitory recording medium having a computer program stored therein for recognizing a plurality of states of a space, the computer program causing a computer to execute:
a first filtering step for performing a filtering process on a time-series signal, which is obtained as a result of performing remote measuring on the space, in accordance with a first cutoff frequency so as to allow a signal component deriving from movement of a biological organism to pass through;
a second filtering step for performing a filtering process on the time-series signal in accordance with a second cutoff frequency, which is lower than the first cutoff frequency, based on biological information of the biological organism;
an amplitude-component extracting step for extracting a first feature quantity related to an amplitude component from a signal passed in the first filtering step and the second filtering step;
a frequency-component extracting step for extracting a second feature quantity related to a frequency component from a signal passed in the first filtering step and the second filtering step;
a model storing step for collecting an aggregate of feature quantity-state data, each piece of the feature quantity-state data including amplitude information corresponding to an output of the amplitude-component extracting unit, frequency information corresponding to an output of the frequency-component extracting unit, and one of the plurality of the sates for the amplitude information and the frequency information; and
a state recognizing step for recognizing a state of the space by using the first feature quantity, the second feature quantity, and the aggregate of feature quantity-state data.

* * * * *